(12) United States Patent
Perez et al.

(10) Patent No.: US 6,642,176 B1
(45) Date of Patent: Nov. 4, 2003

(54) HERBICIDE COMPOSITIONS BASED ON GLYPHOSATES AND ISOXAZOLES

(75) Inventors: Gilbert Antoine Perez, Sathonay Camp (FR); Louis Pillet, Champagne au Mont d'Or (FR); Jean-Claude Febvre, Rillieux la Pape (FR); Sylvie Lavault, Lyons (FR)

(73) Assignee: Bayer CropScience S.A., Lyons (FR)

( * ) Notice: Subject to any disclaimer, the term of this patent is extended or adjusted under 35 U.S.C. 154(b) by 0 days.

(21) Appl. No.: 09/830,866

(22) PCT Filed: Oct. 29, 1999

(86) PCT No.: PCT/FR99/02648

§ 371 (c)(1),
(2), (4) Date: Jul. 30, 2001

(87) PCT Pub. No.: WO00/25584

PCT Pub. Date: May 11, 2000

(30) Foreign Application Priority Data

Nov. 2, 1998 (FR) .............................. 98 13897

(51) Int. Cl.$^7$ ..................... A01N 25/22; A01N 43/80; A01N 57/02
(52) U.S. Cl. .................. 504/128; 504/206; 504/271
(58) Field of Search ................. 504/128, 271, 504/206

(56) References Cited

U.S. PATENT DOCUMENTS 6,069,115 A * 5/2000 Pallett et al. ............... 504/270

FOREIGN PATENT DOCUMENTS

| WO | 90/07275 | * 7/1990 | .......... A01N/57/20 |
|----|----------|----------|----------------------|
| WO | 98/02562 | * 1/1998 | |

OTHER PUBLICATIONS

Turner, D. J. "Effects on glyphosate performance of formulation, additives and mixing with other herbicides". Chapter 15 in The Herbicide Glyphosate, ed. E. Grossbard et al. Butterworths: Boston. p. 221–229. 1985.*

* cited by examiner

*Primary Examiner*—S. Mark Clardy
(74) *Attorney, Agent, or Firm*—Connolly Bove Lodge and Hutz LLP

(57) ABSTRACT

The invention concerns a novel composition comprising a herbicide of the glyphosate family, a herbicide of the isoxazole family and a biological activator, wherein the herbicide of the glyphosate family is selected among N-phosphomethylglycine (glyphosate acid), N-phosphomethylglycine alkaline metal salts, N-phosphomethylglycine ammonium salts and N-phosphomethylglycine trimethyisulphonium salts (sulphosate), and wherein the biological activator consists essentially of an ammonium sulphate. The invention also concerns a method for agronomic treatment of plants tolerant to glyphosate family herbicides and to isoxazole family herbicides to eliminate weeds which consists in applying in a field containing said tolerant plants an appropriate amount of the inventive composition.

24 Claims, No Drawings

HERBICIDE COMPOSITIONS BASED ON GLYPHOSATES AND ISOXAZOLES

This application has been filed under 35 USC 371 as the national stage of international application PCT/FR99/02648, filed Oct. 29, 1999.

The present invention relates to a novel herbicidal composition comprising the combination of two herbicides, a herbicide from the class of the isoxazoles and a herbicide from the glyphosate class, with a biological activator for the herbicide from the glyphosate class. The novel composition of the invention is particularly suitable for application to genetically modified plants in order to render them tolerant to herbicides from the glyphosate class and, where appropriate, in order to render them tolerant also to herbicides from the class of the isoxazoles.

The glyphosate-class herbicides are total systemic herbicides which act within plants by inhibiting an enzyme which is vital to the plants, forming part of the biosynthetic pathway of aromatic amino acids: 5-enolpyruvylshikimate-3-phosphate synthase (EPSPS). There are no known plants with natural tolerance to glyphosate-class herbicides, thereby restricting their use to applications in fields before sowing or to uncultivated areas, such as, for example, railways or roadsides.

The development of the technologies of genetic engineering, and more particularly the technologies of transforming plants by genetic engineering, has made it possible since the 1980s to develop technologies intended for rendering plants, and more particularly crop plants, tolerant to glyphosate-class herbicides. The development of these new technologies made it possible, from 1995 onwards, to market crop plant seeds which are tolerant to glyphosate-class herbicides. The products in question include, in particular, cotton and soya which are sold under the name Roundup Ready (registered trade mark of Monsanto), modified so as to render them tolerant to glyphosate-class herbicides by the introduction of a gene coding for a modified EPSPS. There are other plants which are on the point of being brought onto the market with an identical or different tolerant technology, especially colza and maize, while still other plants are undergoing development.

In the present patent application, the term plants genetically modified in order to render them tolerant to glyphosate-class herbicides will be understood as referring to any plant obtained from a transformed plant whose genome has been modified by genetic engineering in order to render it insensitive to glyphosate-class herbicides. In particular, such plants will have been modified by the introduction of at least one chimeric gene comprising a sequence coding for a glyphosate tolerance enzyme under the control of 5' and 3' heterologous regulatory elements which are functional in plant cells and plants. The glyphosate tolerance enzymes and the chimeric genes useful for their expression in plants in order to render them tolerant to glyphosate-class herbicides are described in particular in the following patents and patent applications: U.S. Pat. No. 4,940,835, U.S. Pat. No. 4,971,908, U.S. Pat. No. 5,145,783, U.S. Pat. No. 5,188,642, U.S. Pat. No. 5,310,677, U.S. Pat. No. 5,312,910, U.S. Pat. No. 5,510,471, U.S. Pat. No. 5,633,435, U.S. Pat. No. 5,627,061, U.S. Pat. No. 5,633,448 and WO 97/04103.

The development of these plants genetically modified to render them tolerant opens up the way to new fields of application of glyphosate-class herbicides together with new technical problems, associated in particular with the application of the herbicide to crop plants without harming them but while maintaining a high level of efficacy on weeds.

In the present patent application, the term plant will be understood to refer to any plant or any photosynthesis-capable differentiated multicellular organism, especially monocotyledons or dicotyledons, more particularly crop plants intended or otherwise for human or animal food, such as maize, wheat, colza, soya, rice, sugar cane, beet, tobacco, cotton, clover, etc., preferably maize or soya, more preferably soya.

Although glyphosate-class herbicides are known to have a broad spectrum of action, they nevertheless have a number of disadvantages, associated with their lack of persistence in the field, and hence an action which is limited over time, and a limited speed of action. To counter these disadvantages, it is known to combine glyphosate-class herbicides, on the one hand, with a herbicide which is more persistent and which has spectrum of action which is complementary to that of the glyphosate-class herbicides and, on the other hand, with a biological activator which will enhance the biological activity of the glyphosate-class herbicides, in particular by promoting the penetration of the herbicide into the leaves, thereby increasing its speed of action. The use of these biological activators, and their combination with other herbicides, has been widely described in the literature (in particular E. Grossbaerd & D. Atkinson, *The Herbicide Glyphosate*, Butterworth & Co. (Publishers) Ltd. 1985).

The isoxazoles are a novel class of herbicides which act on an enzyme involved in the biosynthetic pathway of homogentisate, namely hydroxyphenyl pyruvate dioxygenase (HPPD), whose inhibition leads to whitening of plants sensitive to these herbicides. The isoxazole-class herbicides are described in particular in the following patents and patent applications: EP 418 175, EP 487 357, EP 527 036, EP 560 482, WO 94/14782, U.S. Pat. No. 5,371,064, U.S. Pat. No. 5,371,063, U.S. Pat. No. 5,371,063, U.S. Pat. No. 5,489,064 and U.S. Pat. No. 5,656,573, whose content is incorporated here by reference. These herbicides have a persistent activity and, for certain crops, an action which is complementary to that of glyphosate.

Certain herbicides from this class, such as isoxaflutole, are selective with regard to certain major crop plants and may be employed as they are on plants such as maize. Also known is the means of conferring on the plants improved tolerance to isoxazole-class herbicides by genetic engineering, by introducing into the genome of said plants a gene coding for an HPPD, under the control of 5' and 3' regulatory elements which are functional in plant cells and plants. These genes, which confer improved tolerance to herbicides which are inhibitors of HPPD, and more particularly to isoxazole-class herbicides, are described in particular in the following patent applications: WO 96/38567, FR 97 14569, filed Nov. 17, 1997, and FR 96 16726, filed Dec. 24, 1997. There are even plants known to exhibit a dual tolerance, obtained by genetic engineering, on the one hand to glyphosate-class herbicides and on the other hand to HPPD-inhibitor herbicides, especially those from the class of isoxazoles, which are described in the patent application WO 98/02562.

According to the invention, the term plant tolerant to isoxazole-class herbicides means any plant tolerant to said herbicides, whether naturally tolerant or rendered tolerant following transformation by genetic engineering.

With plants which exhibit properties both of tolerance to glyphosate-class herbicides, obtained from a transformation by genetic engineering, and of tolerance to isoxazole-class herbicides, either natural or obtained from a transformation by genetic engineering, it is possible to apply the herbicides from these two classes simultaneously, not only preemergence but also post-emergence. Such treatments are described in particular in the patent application U.S. Pat. No. 08/969,032, filed Nov. 12, 1997, whose content is incorporated here by reference.

With this aim, attempts were made to develop herbicidal compositions which are easy to use and comprise high concentrations of herbicides from both classes for simultaneous application, and in particular solid compositions which are dilutable or dispersible in water. However, it was found that these formulations had major problems of chemical stability of their constituents, in particular the isoxazole-class herbicides, owing to the presence of particular salts of the glyphosate-class herbicides, in particular the isopropylamine salt of glyphosate, and of certain biological activators necessary to the activity of the glyphosate-class herbicides, in particular the activators most commonly employed in commercial formulations of glyphosate-class herbicides, such as, for example, ethoxylated fatty amines.

The present invention aims to solve this technical problem, allowing the production of a stable concentrated composition of glyphosate-class herbicides and isoxazole-class herbicides, further comprising an appropriate amount of biological activators necessary to the activity of the glyphosate-class herbicides.

The present invention therefore provides a novel composition comprising a herbicide from the glyphosate class, a herbicide from the class of the isoxazoles and a biological activator, wherein the herbicide from the glyphosate class is selected from N-phosphomethylglycine (glyphosate acid), alkali metal salts of N-phosphomethylglycine, ammonium salts of N-phosphomethylglycine and trimethylsulfonium salts of N-phosphomethylglycine (sulfosate), and wherein the biological activator consists essentially of ammonium sulfate.

In one preferred embodiment of the invention, the herbicides from the class of the isoxazoles are selected from the compounds of general formula (I)

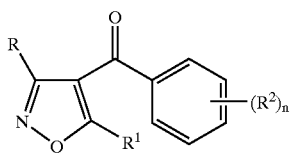

(I)

in which
R is a hydrogen or a radical —$CO_2R^3$;
$R^1$ is a $C_{1-6}$ alkyl radical or a $C_{3-6}$ cycloalkyl radical optionally substituted by a $C_{1-6}$ alkyl radical,
$R^2$ represents independently a halogen, a cyano group, a nitro group, an —$S(O)_pR^6$, —$(CR^4R^5)_qSO_pR^6$, —$NR^7SO_2R^6$, $C_{1-6}$ alkyl, $C_{1-6}$ haloalkyl, $C_{1-6}$ alkoxy or $C_{1-6}$ haloalkoxy radical,
or two groups $R^2$ may together form, on adjacent carbons of the phenyl nucleus to which they are attached, a saturated or unsaturated 5- or 6-membered heterocycle which may contain up to 3 heteroatoms selected from nitrogen, oxygen and sulfur, it being possible for said heterocycle to be substituted by one or more groups selected independently from halogen atoms, the nitro group and —$S(O)_pR^6$, $C_{1-4}$ alkyl, $C_{1-4}$ haloalkyl, $C_{1-4}$ alkoxy or $C_{1-4}$ haloalkoxy radicals, it being understood that the sulfur atoms may be present in the form —SO— or —$SO_2$—,
n is an integer 1, 2, 3, 4 or 5,
p is 0, 1 or 2,
q is 1 or 2, it being understood that, when q is 2, the groups ($CR^4R^5$) may be identical or different,
$R^3$ is a $C_{1-4}$ alkyl radical,
$R^4$ and $R^5$ are independently a hydrogen atom or a $C_{1-4}$ alkyl radical,
$R^6$ is independently a $C_{1-4}$ alkyl radical or a phenyl or benzyl radical, it being possible for each phenyl or benzyl to be substituted by one or more identical or different substituents selected from halogen atoms, the nitro group, —$S(O)_pCH_3$, $C_{1-4}$ alkyl, $C_{1-4}$ haloalkyl, $C_{1-4}$ alkoxy or $C_{1-4}$ haloalkoxy radicals,
$R^7$ is independently a hydrogen atom or a $C_{1-6}$ alkyl radical,
and their agrochemically acceptable salts.

According to the invention, the term agrochemically acceptable salts means the salts of cations or anions which are acceptable for use in the field of agriculture or horticulture, especially the salts known to the person skilled in the art for such a use. Among these salts, mention may be made in particular of the addition salts with a base, including alkali metal salts, especially sodium or potassium salts, alkaline-earth metal salts, especially calcium or magnesium salts, ammonium salts or amine salts, especially diethanolamine, triethanolamine, octylamine, morpholine or dioctylmethylamine salts. Mention may also be made of the addition salts with an acid, including the salts of inorganic acids, especially hydrochlorides, sulfates, phosphates or nitrates and the salts of organic acids, especially acetate.

According to the invention, the term alkyl radical means linear or branched alkyl radicals. $C_{1-4}$ alkyl radicals include the methyl, ethyl, n-propyl, i-propyl, n-butyl, i-butyl and t-butyl radicals. $C_{1-6}$ alkyl radicals additionally include linear or branched pentyl and hexyl radicals. This definition also applies to the alkyl moiety of alkoxy, haloalkyl and haloalkoxy radicals.

According to the invention, the term haloalkyl or ahaloalkoxy radicals means alkyl or alkoxy radicals substituted by at least one halogen atom, including the perhalogenated radicals in which all of the hydrogens of the haloalkyl or haloalkoxy radicals are replaced by identical or different halogens, such as, for example, the trifluoromethyl radical.

According to the invention, the term halogen atom means preferably the atoms of fluorine, chlorine, bromine or iodine.

According to the invention, $C_{3-6}$ cycloalkyl radicals include the radicals cyclopropyl, cyclobutyl, cyclopentyl and cyclohexyl.

Preferably, R is a hydrogen atom or an ethoxycarbonyl radical ($CO_2CH_2CH_3$), and/or $R^1$ is a cyclopropyl radical and/or n is 2 or 3.

When n is 2, the two radicals $R^2$ are preferably in positions 2 and 4 on the benzene ring, and, when n is 3, the three radicals $R^2$ are preferably in positions 2, 3 and 4 on the benzene ring.

Preferably, $R_2$ represents independently a halogen atom, especially chlorine or bromine, or an —$S(O)_pCH_3$, trifluoromethyl, $C_{1-4}$ alkoxy, $C_{1-4}$ haloalkoxy or —$CH_2S$-$(O)_pCH_3$ radical, more preferably a bromine atom or a methylsulfonyl, trifluoromethyl or methylsulfonylmethyl radical.

The compounds of general formula (I) which are particularly preferred in accordance with the invention comprise the following compounds:
5-cyclopropyl-4-(2-methylsulfonyl-4-trifluoromethyl) benzoylisoxazole;
ethyl 5-cyclopropyl-4-(2-methylsulfonyl-4-trifluoromethyl)benzoylisoxazole-3-carboxylate;

ethyl 5-cyclopropyl-4-[3,4-dichloro-2-(methylsulfenyl) benzoyl]isoxazole-3-carboxylate;

5-cyclopropyl-4-[4-bromo-2-(methylsulfonylmethyl) benzoylisoxazole;

5-cyclopropyl-4-(4-methylsulfonyl-2-trifluoromethyl) benzoylisoxazole; and 5-cyclopropyl-4-(4-chloro-2-methylsulfonyl)benzoyl-isoxazole.

According to the invention, the term biological activator consisting essentially of ammonium sulfate means that the biological activator comprises ammonium sulfate alone or ammonium sulfate possibly supplemented by other biological activators in amounts which are suitable for not causing substantial degradation of the isoxazole-class herbicides in the composition of the invention.

According to the invention, the term substantial degradation means a degradation of the isoxazole-class herbicide after 14 days at 54° C. of more than 15% by weight relative to the total weight of isoxazole-class herbicide in the composition (calculated as active substance), advantageously of more than 10% by weight.

Preferably, this suitable amount is less than 30% by weight relative to the total weight of biological activators present in the composition of the invention, more preferably less than 20% by weight, and still more preferably less than 15% by weight.

The other biological activators may be selected among biological activators of glyphosate-class herbicides which are well known to the person skilled in the art and are widely described in the prior art, and their mixtures in any proportions. Preferably, these other biological activators will be selected from ethoxylated (5 to 30 EO) $C_{12-20}$ fatty amines (especially those sold under the names Rhodameen CF/15, CF/15-H, CF/15-B or S35 by Rhodia), ethoxylated (5 to 30 EO) $C_{10-20}$ fatty alcohols (especially those sold under the names Rhodasurf 860/P or Soprophor ASM/30 to M/30 by Rhodia);

alkyl phosphates, especially the alkyl phosphates described in the patent U.S. Pat. No. 5,180,414, whose content is incorporated here by reference, in particular alkyl ($C_{4-12}$) (ethoxy)$_n$ phosphates (n being between 2 and 12), the acid form or its alkali metal salts, especially sodium or potassium salts, or amine salts, especially isopropylamine salts, more particularly the mixtures of alkyl ($C_4$) (ethoxy)$_3$ phosphates and alkyl ($C_{8-10}$) (ethoxy)$_8$ phosphate, in acid form or in the form of sodium, potassium, ammonium or quaternary ammonium salts (especially those sold under the names Geronol ARB/70, CF/Na or CF/AR by Rhodia);

sulfosuccinate hemiesters, especially the sulfosuccinate hemiesters described in the patent application EP 569 264, whose content is incorporated here by reference, in particular the sulfosuccinate hemiesters of $C_{6-12}$ alcohols ethoxylated n times, n being between 1 and 10, preferably between 2 and 6, in the acid form or in the form of alkali metal salts, especially sodium salts, alkaline-earth metal salts, especially calcium salts, and more particularly the disodium hemiester (especially that sold under the name Geropon CF/320 by Rhodia), and sulfosuccinic diesters, especially the optionally ethoxylated (1 to 10 EO) $C_{1-20}$, preferably $C_{6-12}$, alcohol diesters, in the acid form or in the form of alkali metal salts, especially sodium salts, alkaline earth metal salts, especially calcium salts, or substituted or unsubstituted amine salts, in particular sodium dioctylsulfosuccinate (especially that sold under the name Geropon SDS by Rhodia);

betaines (especially under the name Emery 6748 or Velvetex OLB 50 from Henkel), imidazolines (especially under the name Huko25 from Hoechst), arcosinates (especially under the names Hamposyl C, O or L from Hampshire Chemical), alkyl polyglycosides or APGs (especially APG 325 CS or 600 CS from Henkel), ether sulfates (especially Witcolate 1050 or TLS 500 from Witco), ammonium chloride derivatives (especially Emcol CC-RP from Witco) or polyalkoxylated amidoamine derivatives (especially AMAM from Rhodia, as described in the patent application FR 2 737 390).

In one preferred embodiment of the invention, the weight ratio (expressed by weight of active substance) of glyphosate-class herbicide/isoxazole-class herbicide is between 2/1 and 10/1, preferably between 4/1 and 8/1.

Preferably, the total herbicide content, expressed by the weight sum (expressed by weight of active substance) of glyphosate-class herbicides+isoxazole-class herbicides per kilogram of composition, is between 50 g/kg and 900 g/kg, preferably between 200 g/kg and 600 g/kg, more preferably approximately 500 g/kg.

Advantageously, the weight ratio (expressed by weight of active substance) of biological activator/glyphosate-class herbicide is between 1/30 and 3/1, preferably between 1/20 and 2/1, more preferably between 1/5 and 2/1.

The compositions of the invention are preferably solid compositions which may be present in any solid forms known to the person skilled in the art, and more particularly the solid forms which are soluble or dispersible in water, making it possible by dissolution or rapid dispersion in water to obtain a homogeneous aqueous composition suitable for field application by watering or by spraying, by any appropriate means, to the surface of the field and to the crop to be treated.

In order to promote the homogeneous dispersion or dissolution of the essential constituents of the composition of the invention, the person skilled in the art will be able to add all of the appropriate dispersants known from the prior art, subject to the proviso that they do not modify the chemical stability of the essential constituents of this composition, as defined above. Among the customary dispersants, mention may be made in particular of alkylnaphthalenesulfonates or lignosulfonates.

Advantageously, the amount of dispersants (calculated by weight relative to the total weight of the composition) will be less than or equal to 15%, preferably less than or equal to 10%, more preferably between 3 and 8%.

The solid compositions of the invention may be present in particular in the form of powders (WP, WS), granules (SG, WG) or tablets (TB). The powders, granules or tablets of composition of the invention may be obtained by all of the suitable means widely described in the prior art and well known to the person skilled in the art. It is understood that, to the extent that the physical properties of the glyphosate-class herbicides and the isoxazole-class herbicides may vary depending on the chemical composition of the active substance and on the nature of the salts, where appropriate, the person skilled in the art will know to best adapt the customary methods to the specific conditions of use of the herbicides of the invention. Of course, the person skilled in the art will be able to add, where appropriate, any inert carrier, for example silica fillers, necessary to the formulation of the composition of the invention, and also any appropriate additive (antifoam, colorant, tackifier, etc.).

For the compositions in the form of powders or granules, the essential constituents of the composition of the invention may be mixed together before shaping, or shaped separately and then mixed after having been shaped, as indicated for example in the patent application EP 696 168.

The present invention likewise provides a method of agronomically treating plants tolerant to herbicides from the glyphosate class and to herbicides from the class of isoxazoles for the purpose of eliminating weeds, wherein an appropriate amount of the composition of the invention defined hereinabove is applied in a field containing said tolerant plants.

In one preferred embodiment of the invention, the composition of the invention is diluted or dispersed beforehand in an appropriate amount of water.

The compositions of the invention are particularly suitable for allowing the simultaneous application of glyphosate-class herbicides and isoxazole-class herbicides at rates (expressed by weight of active substance) of, for the glyphosate-class herbicides, between approximately 100 g/ha and approximately 1200 g/ha, preferably between approximately 100 g/ha and approximately 800 g/ha, and, for the isoxazole-class herbicides, between approximately 20 g/ha and approximately 500 g/ha, preferably between approximately 40 g/ha and 150 g/ha.

The examples below will illustrate the present invention without, however, seeking to limit its scope.

EXAMPLE 1

Chemical Stability of the Compositions With Different Activators

A number of compositions of extruded granules, comprising an isoxazole-class herbicide, a glyphosate-class herbicide and a number of activators. The compositions are prepared by mixing the various compounds and extruding the mixture, in accordance with the customary techniques of the art. The chemical stability of the isoxazole-class herbicides is evaluated after 14 days at 54° C., measured by the percentage of isoxazole degraded relative to the total weight of isoxazole in the composition prepared initially.

The isoxazole-class herbicides employed for this example, which are representative of herbicides from the class of the isoxazoles, in particular herbicides defined by the general formula (I), are the following:

Compound I: 5-cyclopropyl-4-(2-methylsulfonyl-4-trifluoromethyl)benzoylisozaxole;

Compound II: 5-cyclopropyl-4-[4-bromo-2-(methylsulfonylmethyl)benzoypisoxazole.

The glyphosate-class herbicide representative of the class of herbicides of the glyphosate class that is employed for this example is glyphosate acid.

The adjuvants are as follows: Morwet D425 (dispersant from Witco), Geronol CF/NA on silica (Rhodia), Geropon SDS (Rhodia), Rhodameen S35 (Rhodia) and ammonium sulfate.

The amounts of each constituent are expressed in grams of active substance.

| Composition | 1 | 2 | 3 | C1 |
|---|---|---|---|---|
| Compound I | 63.2 | 63.2 | 63.2 | 63.2 |
| Glyphosate acid | 337 | — | 337 | 337 |
| Glyphosate, ammonium salt | — | 337 | — | — |
| Morwet D425 | 100 | 100 | 50 | 100 |
| Geropon SDS | — | — | 50 | — |
| Rhodameen S35 | — | 503.2 | — | QS 1000 |
| Ammonium sulfate | QS 1000 | QS 1000 | QS 1000 | — |
| % degradation | 2.6 | ? | 8 | 95 |

-continued

| Composition | 4 | 5 | C2 |
|---|---|---|---|
| Compound II | 63.2 | 63.2 | 63.2 |
| Glyphosate | 337 | 337 | 337 |
| Morwet D425 | 50 | 50 | 100 |
| Geronol CF/Na on silica | 20 | 50 | — |
| Geropon SDS | — | — | QS 1000 |
| Ammonium sulfate | QS 1000 | QS 1000 | — |
| % degradation | 2 | 8 | 100 |

The examples above show for the compositions of the invention (compositions 1 to 5) a degradation of the isoxazole-class herbicides of less than 10%, as against 95 to 100% degradation in the absence of ammonium sulfate (controls C1 and C2).

EXAMPLE 2

Disintegrable Tablets

The disintegrable tablets are obtained by the customary techniques of direct tableting of a premix of active substances in the presence of adjuvants customary for this type of formulation, especially disintegrants, fillers or lubricants. The disintegrants are selected in particular from cellulose derivatives, especially crystalline microcelluloses, or derivatives of starches or modified starches. The customary fillers are generally fillers based on silica or silica derivatives, or else sugar derivatives. The customary lubricants are selected in particular from magnesium stearate, sodium benzoate or else talc. The composition may further comprise all customary adjuvants such as preservatives, colorants, fragrances or moisture absorbers.

Two premixes of active substances were prepared, having the compositions below. In these examples of compositions of the invention, the herbicides are firstly the compound I defined in Example I and glyphosate acid. These two herbicides are representative, on the one hand, of all the isoxazole-class herbicides and, on the other hand, of all the glyphosate-class herbicides in accordance with the invention, the teaching of this example not being limited to the two single compounds described.

Premix I:

| Compound I, micronized | 79.79 g |
|---|---|
| Glyphosate, ammonium salt | 476.15 g |
| Ammonium sulfate | 200.00 g |
| Morwett D425 | 50.00 g |

Premix II:

| Compound I, micronized | 79.79 g |
|---|---|
| Glyphosate, ammonium salt | 476.15 g |
| Ammonium sulfate | 200.00 g |
| Morwett D425 | 50.00 g |
| Geronol CF/Na | 66.60 g |

Tablets of the following composition were prepared, the percentages being expressed by weight relative to the total weight of the composition:

|  | Tablets I | Tablets II |
| --- | --- | --- |
| Premix I | 78% | — |
| Premix II | — | 85% |
| Disintegrants | 9% | 8% |
| Filler | 9% | 2% |
| Lubricants | 4% | 5% |

EXAMPLE 3

Biological Activity

Compositions 1 and 2 above were applied to various weed species at rates equivalent to the application of 377 g/ha of glyphosate (expressed as glyphosate acid) and 63.2 g/ha of isoxaflutole (compound 1). The biological efficacy of the compositions of the invention was compared to the application of a mixture prepared in situ (control) of glyphosate (isopropylamine salt, formulation Roundup from Monsanto) and isoxaflutole, corresponding to rates of 560 g/ha of glyphosate (expressed as glyphosate acid) and 50 g/ha of isoxaflutole.

The various species treated are the following: ECHCG (*Echinochloa crus galli*), PANMI (*Panicum miliaceum*), SETFA (*Setaria faberi*), SETVI (*Setaria viridis*), HELAN (*Heliantus annuus*) and SORVU (*Sorghum vulgare*). The measurements of activity are carried out by evaluating the phytotoxicity of the composition on plants 7 days after application (to measure the speed of action) and 22 days after application (to measure the efficacy). The results obtained are reported in the table below.

|  | ECHCG | | PANMI | | SETFA | | SETVI | | HELAN | | SORVU | |
| --- | --- | --- | --- | --- | --- | --- | --- | --- | --- | --- | --- | --- |
|  | 7d | 22d | 7d | 22d | 7d | 22d | 7d | 22d | 7d | 22d | 7d | 22d |
| 1 | 43 | 92 | 73 | 95 | 68 | 98 | 79 | 99 | 50 | 99 | 57 | 90 |
| 2 | 43 | 97 | 70 | 93 | 69 | 98 | 81 | 99 | 43 | 92 | 56 | 90 |
| C | 29 | 100 | 88 | 99 | 72 | 99 | 86 | 99 | 68 | 99 | 55 | 97 |

These results show, for the compositions of the invention, an efficacy and a speed of action which are comparable in all respects with those of the control mixture prepared in situ, whereas the amount of glyphosate in the control mixture is greater than that in the compositions of the invention.

These results confirm that the chemical stability observed in Example 1 for the compositions of the invention is obtained while maintaining the herbicidal properties of the constituents of this composition and therefore its efficacy.

What is claimed is:

1. Composition characterized in that it comprises a herbicide from the glyphosate class, a herbicide from the class of the isoxazoles and a biological activator, wherein the herbicide from the glyphosate class is selected from N-phosphomethylglycine (glyphosate acid), alkali metal salts of N-phosphomethylglycine, ammonium salts of N-phosphomethylglycine and trimethylsulfonium salts of N-phosphomethylglycine (sulfosate), and wherein the biological activator consists essentially of ammonium sulfate.

2. Composition according to claim 1, characterized in that the herbicide from the class of the isoxazoles is selected from the compounds of general formula (I)

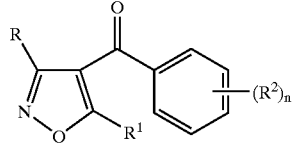

in which
R is a hydrogen or a radical —$CO_2R^3$;
$R^1$ is a $C_{1-6}$ alkyl radical or a $C_{3-6}$ cycloalkyl radical optionally substituted by a $C_{1-6}$ alkyl radical,
$R^2$ represents independently a halogen, a cyano group, a nitro group, an —$S(O)_pR^6$, —$(CR^4R^5)_qSO_pR^6$, —$NR^7SO_2R^6$, $C_{1-6}$ alkyl, $C_{1-6}$ haloalkyl, $C_{1-6}$ alkoxy or $C_{1-6}$ haloalkoxy radical,
or two groups $R^2$ may together form, on adjacent carbons of the phenyl nucleus to which they are attached, a saturated or unsaturated 5- or 6-membered heterocycle which may contain up to 3 heteroatoms selected from nitrogen, oxygen and sulfur, it being possible for said heterocycle to be substituted by one or more groups selected independently from halogen atoms, the nitro group and —$S(O)_pR^6$, $C_{1-4}$ alkyl, $C_{1-4}$ haloalkyl, $C_{1-4}$ alkoxy or $C_{1-4}$ haloalkoxy radicals, it being understood that the sulfur atoms may be present in the form —SO— or —$SO_2$—,
n is an integer 1, 2, 3, 4 or 5,
p is 0, 1 or 2,
q is 1 or 2, it being understood that, when q is 2, the groups ($CR^4R^5$) may be identical or different,
$R^3$ is a $C_{1-4}$ alkyl radical,
$R^4$ and $R^5$ are independently a hydrogen atom or a $C_{1-4}$ alkyl radical,
$R^6$ is independently a $C_{1-4}$ alkyl radical or a phenyl or benzyl radical, it being possible for each phenyl or benzyl to be substituted by one or more identical or different substituents selected from halogen atoms, the nitro group, —$S(O)_pCH_3$, $C_{1-4}$ alkyl, $C_{1-4}$ haloalkyl, $C_{1-4}$ alkoxy or $C_{1-4}$ haloalkoxy radicals,
$R^7$ is independently a hydrogen atom or a $C_{1-6}$ alkyl radical,
and their agrochemically acceptable salts.

3. Composition according to claim 1, characterized in that the herbicide from the class of the isoxazoles is selected from the following compounds:
5-cyclopropyl-4-(2-methylsulfonyl-4-trifluoromethyl) benzoylisoxazole;
ethyl 5-cyclopropyl-4-(2-methylsulfonyl-4-trifluoromethyl)benzoylisoxazole-3-carboxylate;
ethyl 5-cyclopropyl-4-[3,4-dichloro-2-(methylsulfenyl) benzoyl]isoxazole-3-carboxylate;
5-cyclopropyl-4-[4-bromo-2-(methylsulfonylmethyl) benzoylisoxazole;

5-cyclopropyl-4-(4-methylsulfonyl-2-trifluoromethyl) benzoylisoxazole; and 5-cyclopropyl-4-(4-chloro-2-methylsulfonyl) benzoylisoxazole.

4. Composition according to claim 1, characterized in that the biological activator consists of ammonium sulfate alone or ammonium sulfate supplemented by other biological activators in amounts which are suitable for not causing substantial degradation of the isoxazole-class herbicides in the composition of the invention.

5. Composition according to claim 4, characterized in that the suitable amount of other biological activators is less than 30% by weight relative to the total weight of biological activators.

6. Composition according to claim 4, characterized in that the suitable amount of other biological activators is less than 20% by weight relative to the total weight of biological activators.

7. Composition according to claim 4, characterized in that the suitable amount of other biological activators is less than 15% by weight relative to the total weight of biological activators.

8. Composition according to claim 1, characterized in that the weight ratio (expressed by weight of active substance) of glyphosate-class herbicide/isoxazole-class herbicide is between 2/1 and 10/1.

9. A composition according to claim 1, characterized in that the total herbicide content, expressed by the weight sum (expressed by weight of active substance) of glyphosate-class herbicides+isoxazole-class herbicides per kilogram of composition, is between 50 g/kg and 900 g/kg.

10. Composition according to claim 1, characterized in that the weight ratio (expressed by weight of active substance) of biological activator/glyphosate-class herbicide is between 1/30 and 3/1.

11. Composition according to claim 1, characterized in that it is present in solid form.

12. Composition according to claim 1, characterized in that it comprises dispersants.

13. Composition according to claim 12, characterized in that the amount of dispersants (calculated by weight relative to the total weight of the composition) is less than or equal to 15%.

14. Composition according to claim 12, characterized in that the amount of dispersants (calculated by weight relative to the total weight of the composition) is less than or equal to 10%.

15. Composition according to claim 12, characterized in that the amount of dispersants (calculated by weight relative to the total weight of the composition) is between 3 and 8%.

16. Composition according to claim 1, characterized in that the weight ratio (expressed by weight of active substance) of glyphosate-class herbicide/isoxazole-class herbicide is between 4/1 and 8/1.

17. A composition according to claim 1, characterized in that the total herbicide content, expressed by the weight sum (expressed by weight of active substance) of glyphosate-class herbicides+isoxazole-class herbicides per kilogram of composition, is between 200 g/kg and 600 g/kg.

18. A composition according to claim 1, characterized in that the total herbicide content, expressed by the weight sum (expressed by weight of active substance) of glyphosate-class herbicides+isoxazole-class herbicides per kilogram of composition, is approximately 500 g/kg.

19. Composition according to claim 1, characterized in that the weight ratio (expressed by weight of active substance) of biological activator/glyphosate-class herbicide is between 1/20 and 2/1.

20. Composition according to claim 1, characterized in that the weight ratio (expressed by weight of active substance) of biological activator/glyphosate-class herbicide is between 1/5 and 2/1.

21. Method of agronomically treating plants tolerant to herbicides from the glyphosate class and to herbicides from the class of the isoxazoles for the purpose of eliminating weeds, characterized in that an appropriate amount of the composition according to claim 1 is applied in a field containing said tolerant plants.

22. Method according to claim 21, characterized in that the composition is diluted or dispersed beforehand in an appropriate amount of water.

23. Method according to claim 21, characterized in that the glyphosate-class herbicides and the hydroxazole-class herbicides are applied simultaneously at rates (expressed by weight of active substance) of, for the glyphosate-class herbicides, between approximately 100 g/ha and approximately 1200 g/ha, and for the isoxazole-class herbicides, between approximately 20 g/ha and approximately 500 g/ha.

24. Method according to claim 21, characterized in that the glyphosate-class herbicides and the hydroxazole-class herbicides are applied simultaneously at rates (expressed by weight of active substance) of, for the glyphosate-class herbicides, between approximately 400 g/ha and approximately 800 g/ha, and for the isoxazole-class herbicides, between approximately 40 g/ha and 150 g/ha.

* * * * *